United States Patent
Yamada et al.

(10) Patent No.: US 9,688,712 B2
(45) Date of Patent: Jun. 27, 2017

(54) MANUFACTURING METHOD FOR POLYPHENOL COMPOSITION

(71) Applicant: KAO CORPORATION, Chuo-ku (JP)

(72) Inventors: Yasushi Yamada, Narita (JP); Keigo Hanaki, Kamisu (JP); Toshiteru Komatsu, Kamisu (JP)

(73) Assignee: KAO CORPORATION, Chuo-ku (JP)

( * ) Notice: Subject to any disclaimer, the term of this patent is extended or adjusted under 35 U.S.C. 154(b) by 51 days.

(21) Appl. No.: 14/694,317

(22) Filed: Apr. 23, 2015

(65) Prior Publication Data
US 2015/0225440 A1    Aug. 13, 2015

Related U.S. Application Data

(62) Division of application No. 13/703,220, filed as application No. PCT/JP2011/063098 on Jun. 8, 2011, now Pat. No. 9,079,933.

(30) Foreign Application Priority Data

Jun. 9, 2010 (JP) ................................ 2010-131816
Oct. 6, 2010 (JP) ................................ 2010-226574

(51) Int. Cl.
C07H 17/07    (2006.01)
A61K 31/05    (2006.01)
A61K 31/192   (2006.01)
A61K 31/366   (2006.01)
A61K 31/7048  (2006.01)

(52) U.S. Cl.
CPC ............. *C07H 17/07* (2013.01); *A61K 31/05* (2013.01); *A61K 31/192* (2013.01); *A61K 31/366* (2013.01); *A61K 31/7048* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 3,832,475 A | 8/1974 | Zirlin | |
| 4,668,525 A | 5/1987 | Creswick | |
| 2006/0153936 A1 | 7/2006 | Tsuzaki | |
| 2008/0221045 A1 | 9/2008 | Mitsuzumi et al. | |
| 2010/0210589 A1 | 8/2010 | Mitsuzumi et al. | |

FOREIGN PATENT DOCUMENTS

| | | |
|---|---|---|
| EP | 0083570 | 1/1983 |
| EP | 0163420 | 4/1985 |
| JP | 9-252746 | 9/1997 |
| JP | 2000-236856 | 9/2000 |
| JP | 2003-169631 A | 6/2003 |
| JP | 2004-35550 | 2/2004 |
| JP | 2004-065128 | 3/2004 |
| JP | 3549436 | 8/2004 |
| JP | 2007-39419 | 2/2007 |
| JP | 2007-159459 A | 6/2007 |
| JP | 2007-306414 | 11/2007 |
| JP | 2008-271839 | 11/2008 |
| JP | 2009-136225 A | 6/2009 |
| JP | 2012-077051 | 4/2012 |
| WO | 03/090797 A1 | 11/2003 |
| WO | 2005/003112 | 1/2005 |
| WO | 2006/067925 A1 | 6/2006 |

OTHER PUBLICATIONS

Makoto, JP 2007308414, Nov. 29, 2007, machine translation.*
Chang, Pharmaceutical Research, vol. 12, No. 6, 1995.*
Nkhili et al. Phytochem. Anal, vol. 20, pp. 204-415 (2009).
Andersen, Flavonoids: Chemistry, Biochemistry and Applications, CRC Press, p. 239 (2005).
Jackie Chan's Tea, https://web.archive.org/web/20080205015640/http://www.teatech.com/green_tea_recipes.php, obtained via internet archive (Feb. 2008).
Jackie Chan's Tea, InstaGreen Tea, http://www.teatech.com/store/instagreen-tea-100-natural-drink-mix/cat_3.html, downloaded from the internet (Oct. 24, 2014).
The Extended European Search Report issued May 28, 2014, in Application No./ Patent No. 11792462.1-1456 / 2581089 PCT/JP2011/063098.
Office Action issued Dec. 11, 2012, in Japanese Patent Application No. 2011-127371 (with English language translation).
Maeda, H., et al., "Removal of Hesperidin in Satsuma Mandarin (Citrus Ionshiu Marc.) Juice with Adsorbents," Nippon Shokuhin Kogyo Gakkaishi, vol. 32, No. 5, Total 13 Pages (1985) (with computer generated translation).
Xu, G., et al., "Combination of curcumin and green tea catechins prevents dimethylhydrazine-induced colon carcinogenesis," Food and Chemical Toxicology, vol. 48, No. 1, pp. 390-395 (2010).
Kurien, B., et al., "Increasing the solubility of the nutraceutical curcumin by heat and inhibition of oxidative modification," Molecular Nutricion & Food Research, vol. 53, No. 2, p. 308 (2009).
International Search Report Issued Jul. 26, 2011 in PCT/JP11/063098 filed Jun. 8, 2011.

* cited by examiner

*Primary Examiner* — Layla Berry
(74) *Attorney, Agent, or Firm* — Oblon, McClelland, Maier & Neustadt, L.L.P.

(57) ABSTRACT

A method for producing a polyphenol composition including a step of subjecting (A) a hardly water-soluble polyphenol and (B) one or more selected from cathechins, chlorogenic acids and methylated compounds of hardly water-soluble polyphenols to a heat treatment at from 100 to 180° C. in the presence of an aqueous medium.

11 Claims, No Drawings

MANUFACTURING METHOD FOR POLYPHENOL COMPOSITION

This application is a divisional of U.S. application Ser. No. 13/703,220 filed Dec. 10, 2012, which is a National Stage of PCT/JP2011/063098 filed Jun. 8, 2011, both of which are incorporated herein by reference. This application also claims the benefit of JP 2010-131816 filed Jun. 9, 2010 and JP 2010-226574 filed Oct. 6, 2010.

FIELD OF THE INVENTION

The present invention relates to a method for producing a poly phenol composition having an excellent solubility to water.

BACKGROUND OF THE INVENTION

Recently, various materials having a physiological function have been proposed, and many health foods containing these materials have been commercialized. Among them, polyphenols are known to have an antioxidative activity and are acknowledged as an important component of the health foods because of their expected effects such as antiarteriosclerotic, antiallergic and bloodstream enhancement effects.

However, since many polyphenols are hardly soluble to water, it is difficult to use them for aqueous foods such as soft drinks.

Hesperidin, which is a kind of flavonoids and also referred to as vitamin P, is known to be contained in a large amount in the peel of the citrus plants. Hesperidin is widely used for foods, pharmaceuticals or the like, because of its various physiological functions such as enhancement of capillary vessel, prevention of bleeding and regulation of blood pressure. However, although hesperidin dissolves in an alkaline aqueous solution, it hardly dissolves in a neutral to acidic aqueous solution. For example, its solubility in water at 25° C. is as low as 0.02 mg/g.

Then, a technique to solve this problem has been investigated, including a proposal for α-glucosylhesperidin obtained by binding glucose to hesperidin (Patent Document 1). The solubility of α-glucosylhesperidin in water at 25° C. is as high as 200 mg/g or more and it has some advantages such as a function similar to hesperidin.

On the other hand, techniques to solubilize a hardly water-soluble polyphenol into water have been investigated, and various methods have been proposed, including a method for solubilizing the flavonoid compound contained therein by adding a hesperidin glycoside to citrus juice and fruit juice drink followed by heating the mixture (Patent Document 2); a method for making a clathrate of a hardly water-soluble flavonoid and β-cyclodextrin by a heat treatment of them followed by adding α-glucosylhesperidin thereto (Patent Document 3); and a method for solubilizing the flavonoid by mixing a hardly soluble flavonoid and soy bean saponin and/or malonyl isoflavon glycoside in an aqueous medium followed by a heat treatment (Patent Document 4). In these methods, the heat treatment of the hardly water-soluble polyphenols is carried out at around from 70° C. to 90° C.

PRIOR ART DOCUMENT

Patent Document

[Patent Document 1] Japanese Patent No. 3549436
[Patent Document 2] JP-A 2000-236856
[Patent Document 3] JP-A 2008-271839
[Patent Document 4] WO-A 2005/003112

SUMMARY OF THE INVENTION

The present invention relates to the following items (1) to (42).

(1) A method for producing a polyphenol composition containing a step of subjecting (A) a hardly water-soluble polyphenol and (B) one or more selected from the catechins, chlorogenic acids and methylated compounds of hardly water-soluble polyphenols to a heat treatment at from 100 to 180° C. in the presence of an aqueous medium.

(2) The method for producing the polyphenol composition mentioned above, wherein the log P value of (A) the hardly water-soluble polyphenol is from −1.0 to 4.0.

(3) The method for producing the polyphenol composition mentioned above, wherein the log P value of (A) the hardly water-soluble polyphenol is from −0.5 to 3.5.

(4) The method for producing the polyphenol composition mentioned above, wherein (A) the hardly water-soluble polyphenol is one or more selected from hesperidin, quercetin, resveratrol, naringin, curcumin, rutin, caffeic acid and ferulic acid.

(5) The method for producing the polyphenol composition mentioned above, wherein a mass ratio (A)/(B) of (A) the hardly water-soluble polyphenol to (B) one or more selected from the catechins, chlorogenic acids and methylated compounds of hardly water-soluble polyphenols is from 0.005 to 10 in the step of the heat treatment.

(6) The method for producing the polyphenol composition mentioned above, wherein the mass ratio (A)/(B) of (A) the hardly water-soluble polyphenol to (B) one or more selected from the catechins, chlorogenic acids and methylated compounds of hardly water-soluble polyphenols is from 0.01 to 10 in the step of the heat treatment.

(7) The method for producing the polyphenol composition mentioned above, wherein the mass ratio (A)/(B) of (A) the hardly water-soluble polyphenol to (B) one or more selected from the catechins, chlorogenic acids and methylated compounds of hardly water-soluble polyphenols is from 0.02 to 3 in the step of the heat treatment.

(8) The method for producing the polyphenol composition mentioned above, wherein the mass ratio (A)/(B) of (A) the hardly water-soluble polyphenol to (B) one or more selected from the catechins, chlorogenic acids and methylated compounds of hardly water-soluble polyphenols is from 0.168 to 2.33 in the step of the heat treatment.

(9) The method for producing the polyphenol composition mentioned above, wherein the methylated compound of the hardly water-soluble polyphenol is methylhesperidin.

(10) The method for producing the polyphenol composition mentioned above, further containing a step of cooling the reaction solution obtained by the heat treatment and a step of removing solid from the cooled reaction solution.

(11) A polyphenol composition obtained by the producing method mentioned above.

(12) A method for producing a hesperidin composition containing a step of subjecting hesperidin and hesperidin sugar adduct to a heat treatment at from 100 to 180° C. in the presence of an aqueous medium.

(13) The method for producing the hesperidin composition mentioned above, wherein the hesperidin sugar adduct is glucosylhesperidin.

(14) The method for producing the hesperidin composition mentioned above, wherein the hesperidin sugar adduct is monoglucosylhesperidin.

(15) The method for producing the hesperidin composition mentioned above, wherein a mass ratio of hesperidin to hesperidin sugar adduct is from 0.1 to 20 in the step of the heat treatment.

(16) The method for producing the hesperidin composition mentioned above, wherein the mass ratio of hesperidin to hesperidin sugar adduct is from 0.2 to 15 in the step of the heat treatment.

(17) The method for producing the hesperidin composition mentioned above, wherein the mass ratio of hesperidin to hesperidin sugar adduct is from 0.2 to 10 in the step of the heat treatment.

(18) The method for producing the hesperidin composition mentioned above, wherein the mass ratio of hesperidin to hesperidin sugar adduct is from 0.3 to 5 in the step of the heat treatment.

(19) The method for producing the hesperidin composition mentioned above, wherein the mass ratio of hesperidin to hesperidin sugar adduct is from 1.22 to 3 in the step of the heat treatment.

(20) The method for producing the hesperidin composition mentioned above, wherein the aqueous medium is water or an aqueous solution containing alcohol having 4 or less carbon atoms.

(21) The method for producing the hesperidin composition mentioned above, further containing a step of cooling the reaction solution obtained by the heating treatment and a step of removing solid from the cooled reaction solution.

(22) The method for producing the hesperidin composition mentioned above, wherein the cooling rate from the heating temperature to 90° C. is 0.1° C./s or more in the step of cooling the reaction solution.

(23) The method for producing the hesperidin composition mentioned above, wherein the cooling rate from the heating temperature to 90° C. is 0.2° C./s or more in the step of cooling the reaction solution.

(24) The method for producing the hesperidin composition mentioned above, wherein the cooling rate from the heating temperature to 90° C. is 0.5° C./s or more in the step of cooling the reaction solution.

(25) The method for producing the hesperidin composition mentioned above, wherein the cooling rate from the heating temperature to 90° C. is 1° C./s or more in the step of cooling the reaction solution.

(26) The method for producing the hesperidin composition mentioned above, wherein the cooling rate from the heating temperature to 90° C. is 3° C./s or more in the step of cooling the reaction solution.

(27) The method for producing the hesperidin composition mentioned above, wherein the cooling rate from the heating temperature to 90° C. is 5° C./s or more in the step of cooling the reaction solution.

(28) The method for producing the hesperidin composition mentioned above, wherein the cooling rate from the heating temperature to 90° C. is 100° C./s or less in the step of cooling the reaction solution.

(29) The method for producing the hesperidin composition mentioned above, wherein the cooling rate from the heating temperature to 90° C. is 50° C./s or less in the step of cooling the reaction solution.

(30) The method for producing the hesperidin composition mentioned above, wherein a form of the hesperidin composition is an aqueous solution or a powder.

(31) A hesperidin composition wherein a mass ratio of hesperidin to hesperidin sugar adduct is from 0.3 to 10.

(32) The hesperidin composition mentioned above, wherein the mass ratio of hesperidin to hesperidin sugar adduct is from 0.4 to 8.

(33) The hesperidin composition mentioned above, wherein the mass ratio of hesperidin to hesperidin sugar adduct is from 0.5 to 8.

(34) The hesperidin composition mentioned above, wherein the mass ratio of hesperidin to hesperidin sugar adduct is from 1 to 5.

(35) The hesperidin composition mentioned above, wherein a solubility of hesperidin to water at 25° C. is 1.3 g/L or more.

(36) The hesperidin composition mentioned above, wherein the solubility of hesperidin to water at 25° C. is 2 g/L or more.

(37) The hesperidin composition mentioned above, wherein the solubility of hesperidin to water at 25° C. is 3 g/L or more.

(38) The hesperidin composition mentioned above, wherein the solubility of hesperidin to water at 25° C. is 5 g/L or more.

(39) The hesperidin composition obtained by the producing method mentioned above, wherein a mass ratio of hesperidin to hesperidin sugar adduct is from 0.3 to 10.

(40) The hesperidin composition obtained by the producing method mentioned above, wherein the mass ratio of hesperidin to hesperidin sugar adduct is from 0.4 to 8.

(41) The hesperidin composition obtained by the producing method mentioned above, wherein the mass ratio of hesperidin to hesperidin sugar adduct is from 0.5 to 8.

(42) The hesperidin composition obtained by the producing method mentioned above, wherein the mass ratio of hesperidin to hesperidin sugar adduct is from 1 to 5.

EMBODIMENT FOR CARRYING OUT THE INVENTION

A production process of hesperidin glycoside such as α-glucosylhesperidin is complex and expensive. Therefore, it is not economically favorable to use hesperidin glycoside in place of hesperidin or as a solubilizing agent. In addition, use of a solubilizing agent such as malonyl isoflavon glycoside may cause a problem of limited application due to a peculiar grain smell of the solubilizing agent derived from soy bean, although a solubility of hardly water-soluble polyphenol may be increased. Furthermore, only the hesperidin composition with low content of hesperidin has been obtained, and the method for sufficiently dissolving hesperidin has not been known yet.

Thus, the present invention relates to providing a method for producing a polyphenol composition having an excellent solubility to water using a material with low cost and less influence on the taste and flavor of the composition.

In addition, the present invention relates to providing a hesperidin composition having a high content of hesperidin and the excellent solubility, as well as a method for producing the hesperidin composition.

As a result of extensive investigation on the solubilizing technique for hardly water-soluble polyphenols, the present inventors found that the solubility of hardly water-soluble polyphenols drastically increases by heating the hardly water-soluble polyphenols and the catechins, chlorogenic acids or a methylated product of hardly water-soluble polyphenols at 100° C. or higher in the presence of an aqueous medium, and that the composition subjected to this treatment suppresses the precipitation of the hardly water-soluble polyphenols and maintains high solubility even at room temperature. Furthermore, the inventors found that the influence of the catechins, chlorogenic acids or the methylated product of hardly water-soluble polyphenols on the taste and flavor of the composition is small.

Furthermore, as a result of extensive investigation on the solubilizing technique for hesperidin, the present inventors have found that the solubility of hesperidin drastically increases by heating hesperidin and hesperidin sugar adduct at 100° C. or higher in the presence of an aqueous medium, and that the composition subjected to this treatment suppresses the precipitation of hesperidin and maintains high solubility of hesperidin even at room temperature.

According to the present invention, a polyphenol composition having the excellent solubility to water can be provided at low cost. The polyphenol composition of the present invention is useful for various foods and drinks and pharmaceuticals because the influence of the solubilizing agent on the taste and flavor is small.

Furthermore, according to the present invention, the solubility of hesperidin to water or the like can be increased and the hesperidin composition having the excellent solubility regardless of high content of hesperidin can be provided.

The method for producing the polyphenol composition according to the present invention includes the step of subjecting (A) a hardly water-soluble polyphenol and (B) one or more selected from cathechins, chlorogenic acids and methylated compounds of hardly water-soluble polyphenols to a heat treatment at from 100 to 180° C. in the presence of an aqueous medium. Hereafter, "one or more selected from the catechins, chlorogenic acids and methylated compounds of hardly water-soluble polyphenols" is also simply referred to as a component "B". The method for producing the polyphenol composition is also referred to as the first method.

The term "hardly water-soluble polyphenols" herein means the polyphenols having a log P value of from −1.0 to 4.0. The hardly water-soluble polyphenols preferably have a log P value of from −0.5 to 3.5. The log P value is a common logarithm of the partition coefficient between 1-octanol, and water and an index indicative of a hydrophobicity of an organic compound. Larger positive log P value indicates larger hydrophobicity. The log P value of the polyphenols may be measured according to the flask shaking method in accordance with JIS Z7260-107. The details are described in Examples.

Preferably applicable (A) hardly water-soluble polyphenols include phenolic substances having one or more, or in particular two or more hydroxyl groups connected to a benzene ring, for example, a flavonoid derived from plant, tannin, phenolic acid or the like. Examples of the hardly water-soluble polyphenols more preferably applicable include flavonols, flavanones, flavones, isoflavones, phenol carboxylic acids or the like.

Specific examples include rutin, quercitrin, isoquercitrin, quercetin, myricitrin, daidzein, daidzin, glycitein, glycitin, genistein, genistin, myricetin, hesperidin, neohesperidin, hesperetin, naringin, curcumin, ringenin, prunin, astragalin, kaempferol, resveratrol, apiin, apigenin, delphinidin, delphin, nasunin, peonidin, peonin, petunin, malvidin, malvin, enin, cyanidin, leukocyanidin, cyanine, chrysanthemine, keracyanin, idaein, mecocyanin, pelargonidin, callistephin, caffeic acid, ferulic acid, p-coumaric acid or the like. Among them, rutin, quercetin, hesperidin, naringin, curcumin, resveratrol, caffeic acid and ferulic acid are preferable. The hardly water-soluble polyphenols may be a single substance or a mixture of two or more substances.

The catechins used in the present invention is a generic term, which encompasses non-epi-form catechins such as catechin, gallocatechin, catechin gallate and gallocatechin gallate, and epi-form catechins such as epicatechin, epigallocatechin, epicatechin gallate and epigallocatechin gallate. A content of the catechins is defined based on the total amount of 8 types mentioned above.

As the catechins, a tea extract may be used. As the tea extract, at least one selected from tea extract solution, the concentrate thereof and the purified product thereof may be used.

The "tea extract solution" herein means the extract solution from tea leaves with a hot water or a water-soluble organic solvent, neither concentrated nor purified. As the water-soluble organic solvent, for example, lower alcohols such as ethanol may be used. As the extraction method, known methods such as kneader extraction, stirring extraction (batch extraction), counter-current extraction (drip extraction), column extraction or the like may be used.

Tea leaves used for extraction may be roughly classified into a non-fermented tea, a semi-fermented tea and a fermented tea depending on the processing method. As the non-fermented tea, green tea such as sencha, bancha, gyokuro, tencha, kamairicha, kukicha, boucha, mecha, is exemplified. As the semi-fermented tea, oolong tea such as tekkannon, shikishu, golden cassia, wuyi rock tea, is exemplified. Further, as fermented tea, black teas such as Darjeeling, Assam and Ceylon is exemplified. These teas may be used either singly or in combination of two or more. Of these, green teas are preferred from the standpoint of the content of the catechins.

The term "concentrate of tea extract solution" means one obtained, from a solution which has been extracted from tea leaves selected from non-fermented tea, semi-fermented tea and fermented tea with hot water or a water-soluble organic solvent, with the catechins at a concentration raised by removing a part of water, and can be prepared, for example, by the method disclosed in JP-A-59-219384, JP-A-04-020589, JP-A-05-260907, JP-A-05-306279 or the like. The form thereof includes solid, aqueous solution, slurry or the like. Commercial products of the concentrated tea extract solution may be used, including, the concentrated green tea extract solution such as "POLYPHENON" (product of Mitsui Norin Co., Ltd.), "TEAFURAN" (product of ITO EN, LTD.), "SUNPHENON" (product of Taiyo Kagaku Co., Ltd.).

A purification of the tea extract solution or the like may be carried out using a solvent and a column.

Chlorogenic acids used in the present invention is a generic term, which collectively encompasses mono-caffeoylquinic acids including 3-caffeoylquinic acid, 4-caffeoylquinic acid and 5-caffeoylquinic acid, monoferuloylquinic acids including 3-feruloylquinic acid, 4-feruloylquinic acid and 5-feruloylquinic acid and dicaffeoylquinic acids including 3,4-dicaffeoylquinic acid, 3,5-dicaffeoylquinic acid and 4,5-dicaffeoylquinic acid. A content of chlorogenic acids is defined based on the total amount of 9 types mentioned above.

In addition, chlorogenic acids may be in the form of a salt including, for example, a salt with an alkaline metal such as sodium, potassium, a salt with an alkaline earth metal such as magnesium, calcium, a salt with an organic amine such as monoethanolamine, diethanolamine, triethanolamine, and a salt with a basic amino acid such as arginine, lysine, histidine, ornithine.

As chlorogenic acids, the plant extract containing this, the concentrate thereof, the purified product thereof or the like may be used. As such plant extract, for example, extract from sunflower seed, unripe apple fruit, green coffee bean, simon leaves, strobile of pine family plant, seed husk of pine family plant, leaves of sugarcane nandina, burdock, peel of eggplant, fruit of Japanese plum, coltsfoot, vitaceae family plant or the like is exemplified. Among them, green coffee bean extract is preferable in view of a content of chlorogenic acids or the like. As for the kind of coffee tree, any of Coffee Arabica, Coffee Robusta, Coffee Liberica and Coffee Arabusta may be used. Methods and conditions for extraction, concentration and purification are not particularly limited, and known methods and conditions may be used.

As the chlorogenic acids, commercially available chlorogenic acid-containing preparation such as, for example, Flavor Holder RC (T. Hasegawa Co., Ltd.) may also be used.

The methylated product of the hardly water-soluble polyphenols used in the present invention is obtained by methylation of the hardly water-soluble polyphenols mentioned above to solubilize it in water. A position and a number of the methylation are not particularly limited. Specifically, methylhesperidin, methylquercetin, methylresveratrol, methylrutin or the like are exemplified, among which methylhesperidin is preferable. It is known that methylhesperidin mainly includes chalcone-type compound (A) and flavanone-type compound (B). As its structural component, the following are exemplified.

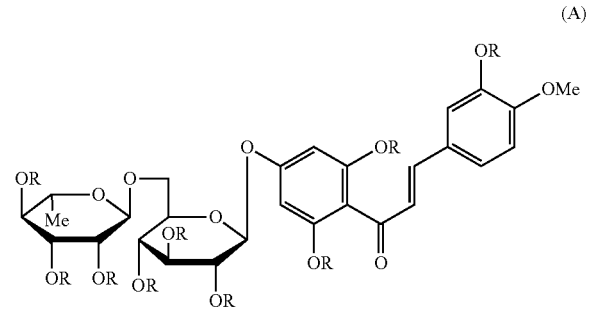

(A)

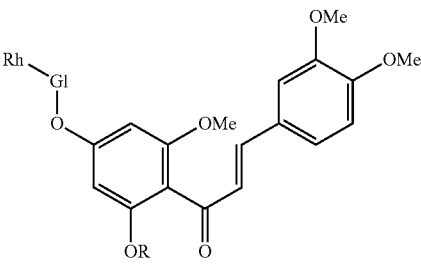

(C)

| | R | Gl-2 | Rh-2 |
|---|---|---|---|
| (C-1) | Me | Me$_2$ | H |
| (C-2) | H | Me | H |
| (C-3) | H | H | H |

(D)

| | R | Gl-2 | Rh-2 |
|---|---|---|---|
| (D-1) | H | Me | Me |
| (D-2) | H | Me | H |
| (D-3) | H | H | H |

(wherein Gl and Rh represent a glucose residue and a rhamnose residue, respectively. Gl-2 and Rh-2 represent 2-position of the glucose residue (In the case of C-1,3-position is also included.) and 2-position of the rhamnose residue, respectively.)

Hesperidin methylchalcone as a raw material for cosmetics is used as a compound represented by (E). It is noted that the composition which contains a large amount of chalcone type compound is also referred to as hesperidin methylchalcone.

(B)

(E)

(wherein R represents a hydrogen atom or a methyl group.)

It is noted that methylhesperidin as a pharmaceutical additive and a food additive is mainly used as a mixture of the compound (C) and compound (D).

(wherein R represents a hydrogen atom or a methyl group.)

Methylhesperidin used in the present invention may contain both of the chalcone-type compound (A) and the flavanone-type compound (B) mentioned above or may contain either of them.

A more preferable methylhesperidin in the present invention is a mixture of the compound (C) and the compound (D).

Methylhesperidin may be produced in accordance with a commonly known method, for example, by dissolving hesperidin in an aqueous solution of sodium hydroxide, allowing the alkaline solution thereof to react with a corresponding amount of dimethylsulfuric acid, neutralizing the reaction solution with sulfuric acid, extracting the mixture with n-butyl alcohol, and evaporating the solvent therefrom, followed by recrystallization using isopropyl alcohol (Sakieki, Nippon Kagaku Zassi, 79, 733-6 (1958)). The production method is not limited to this one.

A commercially available methylhesperidin-containing preparation may be used as methylhesperidin, including, for example, "Methyl hesperidin" (Tokyo Chemical Industry Co., Ltd.), "Hesperidin methylchalcone" (Sigma Co.) and "Methylhesperidin" (Hamari Chemicals Ltd.).

In the present invention, the catechins, chlorogenic acids or methyl hesperidin may be used alone or in combination of two or more as the component (B).

The production method of the hesperidin composition according to the present invention includes the step of subjecting hesperidin and hesperidin sugar adduct to a heat treatment at from 100 to 180° C. in the presence of an aqueous medium. This producing method of the hesperidin composition is also referred to as the second method.

Hesperidin is a compound in which rutinose (L-rhamnosyl ($\alpha 1 \rightarrow 6$)-D-glucose) is connected to a hydroxyl group at 7-position of hesperetin (5,7,3'-trihydroxy-4'-methoxyflavanone) via a $\beta$-bonding.

Hesperidin sugar adduct is a compound composed of hesperidin with from 1 to 10 sugars further bonded. Examples of the sugar include glucose, maltose, fructose, rhamnose, lactose or the like. Among them, glucosylhesperidin composed of hesperidin with from 1 to 10 glucose units bonded is preferable in view of its solubility and solubilizing power, monoglucosylhesperidin with one glucose unit bonded being more preferable. In addition, a number of glucose added may have a distribution. Preferred average mole number of glucose added relative to 1 mole of hesperidin is from 1 to 10. It should be noted that hesperidin itself is a glycoside of hesperetin as an aglycone with sugar bonded as mentioned above. In order to distinguish from this in the present invention, the compound of hesperidin with sugar further bonded is referred to as hesperidin sugar adduct.

These hesperidin and hesperidin sugar adduct may be industrially produced by a commonly known method utilizing a chemical synthesis and an enzymatic reaction. In addition, hesperidin may be obtained by an extraction from a natural product containing this, preferably from a plant. These substances are also manufactured and sold as a reagent or the like. Examples of the commercially available hesperidin include Hesperidin "Hamari" from Hamari Chemicals Ltd. Examples of the commercially available hesperidin sugar adduct include "Hayashibara Hesperidin S" from Hayashibara Biochemical Laboratories, Inc.

The aqueous medium used in the present invention includes water and an aqueous solution of an organic solvent. Tap water, distilled water, ion exchange water and purified water are exemplified as water. The organic solvent is not particularly limited so long as the solvent is homogeneously mixed with water. As the organic solvent, an alcohol having 4 or less carbon atoms is preferable, methanol and ethanol being more preferable, and ethanol being even more preferable because it is applicable for food. A concentration of the organic solvent in the aqueous solution is preferably from 0.1 to 80 mass % (hereafter simply denoted by "%"), more preferably from 1 to 70%, more preferably from 5 to 60%, even more preferably from 20 to 50%.

It is preferable to use an aqueous solution of an organic solvent as the aqueous medium because the content of hesperidin in the hesperidin composition obtained may be increased.

In addition, the aqueous medium used in the present invention may contain a solute. The solute is not particularly limited, and an acid such as amino acid, an inorganic salt, an organic salt, sugar or the like may be exemplified. Soy sauce, ponzu sauce, basting, fruit juice, vegetable juice, coffee, tea or the like may be used.

Since the solubility of (A) hardly water-soluble polyphenols to water is low, it is preferable to disperse this into the aqueous medium to exist in the form of slurry.

The content of (A) hardly water-soluble polyphenols in the aqueous medium in the first method depends on a type of the hardly water-soluble polyphenols. Usually, it is preferably from 0.1 to 100 g/L, more preferably from 0.5 to 50 g/L, more preferably from 0.7 to 20 g/L, even more preferably from 0.72 to 10 g/L in view of fluidity.

On the other hand, the component (B) of the present invention is used preferably as solution thereof in an aqueous medium. A content of the component (B) in the aqueous medium is preferably from 0.1 to 200 g/L, more preferably from 0.5 to 100 g/L, more preferably from 1 to 50 g/L, even more preferably from 4.28 to 4.31 g/L in view of fluidity.

In the first method, a mass ratio ((A)/(B)) of (A) hardly water-soluble polyphenols to the component (B) in the aqueous medium is preferably from 0.005 to 10, more preferably from 0.01 to 10, more preferably from 0.02 to 3, even more preferably from 0.168 to 2.33 in view of solubility of the polyphenol composition obtained after heat treatment and cooling.

A content of hesperidin in the aqueous medium in the second method is preferably from 0.1 to 100 g/L, more preferably from 0.5 to 50 g/L, more preferably from 1 to 20 g/L, even more preferably from 4 to 18 g/L in view of fluidity.

Hesperidin sugar adduct is used preferably in as a solution thereof in an aqueous medium. A content of hesperidin sugar adduct in the aqueous medium is preferably from 0.1 to 200 g/L, more preferably from 0.5 to 100 g/L, more preferably from 1 to 50 g/L, even more preferably from 5 to 20 g/L in view of fluidity.

In the second method, a mass ratio of hesperidin to hesperidin sugar adduct in the aqueous medium is preferably from 0.1 to 20, more preferably from 0.2 to 15, more preferably from 0.2 to 10, more preferably from 0.3 to 5, even more preferably from 1.22 to 3 in view of solubility of the hesperidin composition obtained after heat treatment and cooling.

The method of subjecting (A) hardly water-soluble polyphenols and the component (B) to a heat treatment, and the method of subjecting hesperidin and hesperidin sugar adduct to a heat treatment in the presence of an aqueous medium are not particularly limited, and a commonly known method may be applied.

A temperature of heat treatment is from 100 to 180° C., more preferably from 110 to 170° C., more preferably from 120 to 160° C., even more preferably from 120 to 150° C. in view of an enhancement of solubility and a heat stability of the hardly water-soluble polyphenols. Heating means include, for example, steam and electricity.

A pressure for the heat treatment is preferably from 0 to 10 MPa in gauge pressure, more preferably from 0.1 to 8 MPa, more preferably from 0.1 to 6 MPa, more preferably from 0.2 to 6 MPa, more preferably from 0.2 to 4 MPa, more preferably from 0.25 to 2 MPa, more preferably from 0.3 to 1.5 MPa, even more preferably from 0.3 to 0.6 MPa. The pressure is preferably set at the saturated vapor pressure of water or higher. Gas may be used for pressurization. Examples of the gas used include inert gas, steam, nitrogen gas, helium gas or the like. Pressurization may be regulated by a back pressure valve without a gas.

Heat treatment may be carried out using any method including, for example, batch method, semi-batch method, flow-type reaction method or the like. Among them, flow-type reaction method is preferable because the reaction time is easily regulated.

A time of heat treatment is preferably from 0.1 to 30 min, more preferably from 0.2 to 15 min, even more preferably from 0.5 to 8 min after the aqueous medium has reached the set temperature in view of an enhancement of solubility and a heat stability of the hardly water-soluble polyphenols.

In the case of the flow-type reaction method, the time of the heat treatment is defined as the average residence time calculated from the volume of the high temperature and high pressure part in the reactor divided by the supply rate of the aqueous medium.

In the case of the flow-type reaction method, the flow rate of the aqueous medium depends on the volume of the reactor. If the volume of the reactor is 100 mL, it is preferably from 3.3 to 200 mL/min, more preferably from 6.7 to 150 mL/min.

After the heat treatment, it is preferable that the reaction solution obtained by the heat treatment is cooled to 90° C. or lower, preferably 50° C. or lower, more preferably 30° C. or lower. The lower limit of cooling is 0° C. or higher, preferably 10° C. or higher, so that the reaction solution does not freeze. The reaction solution may be mixed and stirred for from 0.5 to 5 days, preferably from 1 to 3 days while cooling. In addition, when a solid composition is to be obtained, the reaction solution may be subjected to a freeze-drying.

The cooling rate of the reaction solution, which is calculated from the time required for lowering the temperature from the heat treatment temperature to 90° C., is 0.1° C./s or more, more preferably 0.2° C./s or more, more preferably 0.5° C./s or more, more preferably 1° C./s or more, more preferably 3° C./s or more, even more preferably 5° C./s or more. The solubility may be improved by larger cooling rate. Therefore, although the upper limit of the cooling rate is not particularly determined, it is preferably, for example, 100° C./s or less, more preferably 50° C./s or less.

In addition, it is preferable to remove solid from the reaction solution in order to increase the solubility of the composition obtained. The method to remove the solid is not particularly limited, and is carried out, for example, by a centrifugation, a decantation or a filtration.

Although the polyphenol composition obtained by the first method has a high content of the hardly water-soluble polyphenols, a precipitation of the hardly water-soluble polyphenols is suppressed even at room temperature and the composition has the excellent solubility to water. In addition, the influence of the catechins, chlorogenic acids or methylated product of hardly water-soluble polyphenols on the taste and flavor of the composition is small. Therefore, the polyphenol composition according to the present invention is applicable to various foods and drinks and pharmaceuticals or the like. It is especially useful for packed beverage. Examples of the packed beverage include a tea beverage such as green tea and a non-tea based beverage such as sport drink, isotonic drink, near water, or the like.

Although the reason why the solubility of the hardly water-soluble polyphenols can be increased by the heat treatment of (A) hardly water-soluble polyphenols and the component (B) at 100° C. or higher is not clear, it is assumed as follows in accordance with the UV spectrum analysis. It is supposed that the hardly water-soluble polyphenols, the catechins, chlorogenic acids and methylated product of hardly water-soluble polyphenols are solved in water by a self-association of each molecule having a structure in which the hydrophobic portion is laminated and the hydrophilic portion is faced outside, although there is a difference in the solubility among the components. When heated at 100° C. or higher in the state that the both components co-exist in the aqueous medium, the laminate structure may be collapsed and disintegrated, causing the interaction between the hardly water-soluble polyphenols and the component (B) to form a new laminate structure containing the hardly water-soluble polyphenols and the component (B) intermixed. The solubility of the hardly water-soluble polyphenols may be drastically enhanced because the new laminate structure is maintained after cooling.

A content of (A) hardly water-soluble polyphenols in the polyphenol composition obtained by the first method depends on a type of the hardly water-soluble polyphenol, and it is preferably from 0.1 to 70%, more preferably from 0.2 to 50%.

Although the hesperidin composition obtained by the second method has a high content of hesperidin, precipitation of hesperidin is suppressed at room temperature, and the composition has the excellent solubility.

A solubility of hesperidin of the hesperidin composition is preferably 1.3 g/L or more, more preferably 2 g/L or more, more preferably 3 g/L or more, even more preferably 5 g/L or more. The solubility herein means the solubility to water at 25° C.

It has been previously known that α-glucosylhesperidin may be used as the solubilizing agent for hesperidin. The solubilizing effect of α-glucosylhesperidin has been limited, as described in Patent Document 3. Therefore, the above-mentioned effect by the heat treatment at 100° C. or higher is considered to be a surprising effect which is not expected from the conventional techniques.

Although the reason why the above-mentioned problem can be solved by the heat treatment of hesperidin and hesperidin sugar adduct at 100° C. or higher is not clear, it is assumed as follows in accordance with the UV spectrum analysis. It is supposed that hesperidin and hesperidin sugar adduct are solved in water by a self-association of each molecule having a structure in which the hydrophobic portion is laminated and the hydrophilic portion is faced outside, although there is a difference in the solubility between both components. When heated at 100° C. or higher in the state that the both components co-exist in the aqueous medium, the laminate structure may be collapsed and disintegrated, causing the interaction between hesperidin and hesperidin sugar adduct to form a new laminate structure containing hesperidin and hesperidin sugar adduct intermixed. The solubility of hesperidin may be drastically enhanced because the new laminate structure is maintained after cooling.

A mass ratio of hesperidin to hesperidin sugar adduct in the hesperidin composition is from 0.3 to 10, preferably from 0.4 to 8, more preferably from 0.5 to 8, even more preferably from 1 to 5.

A form of the polyphenol composition and the hesperidin composition according to the present invention may be an aqueous solution, or a paste prepared by adjusting the content of water. In addition, the composition may be in a state of solid such as powder, granule, or solid by removing water. Means to adjust or remove the content of water include freeze-drying, evaporation, spray-drying or the like.

EXAMPLES

[Measurement for Hardly Water-Soluble Polyphenols, Methylhesperidin and Hesperidin Sugar Adduct]

A measurement for hardly water-soluble polyphenols, methylhesperidin and hesperidin sugar adduct was performed using High Performance Liquid Chromatograph manufactured by Hitachi, Ltd. equipped with a column Cadenza CD-C18 (4.6 mmϕ×150 mm, 3 μm) manufactured by Intact Co. at a column temperature of 40° C., in accordance with the gradient method. A mobile phase, Solution A, was 0.05 mol/L acetic acid aqueous solution, and another mobile phase, Solution B, was acetonitrile. Flow rate was 1.0 mL/min. Gradient condition was as follows.

| Time (min) | Solution A (%) | Solution B (%) |
|---|---|---|
| 0 | 85 | 15 |
| 20 | 80 | 20 |
| 35 | 10 | 90 |
| 50 | 10 | 90 |
| 50.1 | 85 | 15 |
| 60 | 85 | 15 |

Sample injection volume was 10 μL. Rutin and methylhesperidin were determined by absorbance at a wavelength of 360 nm. Ferulic acid and caffeic acid were determined at 320 nm. Curcumin was determined at 425 nm. Other hardly water-soluble polyphenols and hesperidin sugar adduct were determined at 283 nm.

[Measurement of Log P Value of the Hardly Water-Soluble Polyphenols]

The measurement was performed in accordance with the flask shaking method described in JIS Z7260-107. First, 1-octanol and distilled water were shaken for 24 hours at 25° C. to equilibrate them. Then, 10 mg of polyphenol was weighed into a glass vial with a cap, into which each of 4 mL of the equilibrated 1-octanol and water was added. The vial was shaken for 4 days at 25° C. The phases of 1-octanol and water were separated by centrifugation, and the concentration of polyphenols in each phase was determined by HPLC similarly to the above-mentioned "Measurement for hardly water-soluble polyphenols". Log P value is a common logarithm of the partition coefficient between the two phases.

[Measurement for the Catechins]

Samples were diluted with distilled water as needed, and were measured using a High Performance Liquid Chromatograph (Type SCL-10AVP) manufactured by Shimadzu Corporation equipped with a packed column for liquid chromatography L-Column TMODS (4.6 mmϕ×250 mm: manufactured by Judicial Foundation Chemicals Evaluation and Research Institute, Japan), with a column temperature of 35° C., in accordance with the gradient method. A mobile phase, Solution A, was a distilled water solution of 0.1 mol/L acetic acid, and another mobile phase, Solution B, was an acetonitrile solution of 0.1 mol/L acetic acid. Sample injection volume was 20 μL, and the wavelength of UV detector was 280 nm.

(Concentration Gradient Condition)

| Time (min) | Solution A (%(v/v)) | Solution B (%(v/v)) |
|---|---|---|
| 0 | 97 | 3 |
| 5 | 97 | 3 |
| 37 | 80 | 20 |
| 43 | 80 | 20 |
| 43.5 | 0 | 100 |
| 48.5 | 0 | 100 |
| 49 | 97 | 3 |
| 62 | 97 | 3 |

[Measurement for Chlorogenic Acids]
(Analysis Apparatuses)

HPLC (manufactured by Hitachi, Ltd.) was used. Model numbers of the component units of the apparatuses are as follows.
Solution sending unit (degasser included): L-2130
Autosampler (with cooler): L-2200
Column oven: L-2300
Separation column: Cadenza CD-C18, Size: 4.6 mm i.d.× 150 mm, 3 μm (Intact Co.)
Detector (UV-visible spectrophotometer): L-2420
(Analysis Conditions)
Sample injection volume: 10 μL
Flow rate: 1.0 mL/min
Detection wavelength of UV spectrophotometer: 325 nm (for chlorogenic acids)
Eluent A: 5% acetonitrile containing 0.05 mol/L acetic acid, 0.01 mol/L sodium acetate, and 0.1 mmol/L HEDPO
Eluent B: acetonitrile
(Concentration Gradient Condition)

| Time (min) | Solution A (% (v/v)) | Solution B (% (v/v)) |
|---|---|---|
| 0 | 100 | 0 |
| 10 | 100 | 0 |
| 15 | 95 | 5 |
| 20 | 95 | 5 |
| 22 | 92 | 8 |
| 50 | 92 | 8 |
| 52 | 10 | 90 |
| 60 | 10 | 90 |
| 60.1 | 100 | 0 |
| 70 | 100 | 0 |

Example 1

Each of a hesperidin preparation (Hesperidin "Hamari" (trade name), manufactured by Hamari Chemicals Ltd., hesperidin content 90%, the same shall apply hereafter) and an epigallocatechin gallate (EGCG) preparation (TEAVIGO manufactured by DMS Nutritional Products Co., EGCG content 100%, the same shall apply hereafter) was dispersed at a concentration of 10 g/L and dissolved at a concentration of 4.29 g/L, respectively, in distilled water, and homogeneously stirred in a slurry supply tank. The solution in the slurry supply tank was fed to a stainless steel flow-type reactor with inner volume of 100 mL (manufactured by Nitto Koatsu Co., Ltd.) at a flow rate of 100 mL/min, and the reaction was carried out at 120° C. (average residence time 1 minute). Pressure was adjusted to 0.3 MPa (gauge pressure) by an outlet valve. Reaction solution was taken out through the reactor outlet, cooled to room temperature (25° C.) and recovered. The recovered solution was stirred by shaking for 3 days at room temperature. After shaking, solid were filtered off to obtain the hesperidin composition as a hesperidin-containing aqueous solution. Reaction conditions and the measurement result of a concentration of hesperidin and EGCG in the composition are shown in Table 1.

Example 2

A hesperidin composition was obtained as a hesperidin-containing aqueous solution by a same procedure as in Example 1, except that the reaction temperature was 110° C. Reaction conditions and the measurement result of a concentration of hesperidin and EGCG in the composition are shown in Table 1.

Comparative Examples 1 and 2

A hesperidin composition was obtained as a hesperidin-containing aqueous solution by a same procedure as in Example 1, except that the reaction temperature was 90° C. or 70° C. and the gauge pressure was 0 MPa. Reaction conditions and the measurement result of a concentration of hesperidin and EGCG in the composition are shown in Table 1.

Example 3

A hesperidin composition was obtained as a hesperidin-containing aqueous solution by a same procedure as in Example 1, except that a purified coffee bean extract (chlorogenic acids content 40%, the same shall apply hereafter) was used as the chlorogenic acids at a concentration of 10.7 g/L. Reaction conditions and the measurement result of a concentration of hesperidin and chlorogenic acids in the composition are shown in Table 1.

Comparative Example 3

A hesperidin composition was obtained as a hesperidin-containing aqueous solution by a same procedure as in Example 3, except that the reaction temperature was 70° C. and the gauge pressure was 0 MPa. Reaction conditions and the measurement result of a concentration of hesperidin and chlorogenic acids in the composition are shown in Table 1.

Example 4

A hesperidin composition was obtained as a hesperidin-containing aqueous solution by a same procedure as in Example 1, except that a methylhesperidin preparation (manufactured by Hamari Chemicals Ltd., methylhesperidin content 100%, the same shall apply hereafter) was used instead of the EGCG preparation. Reaction conditions and the measurement result of a concentration of hesperidin and methylhesperidin in the composition are shown in Table 1.

Example 5

A hesperidin composition was obtained as a hesperidin-containing aqueous solution by a same procedure as in Example 4, except that the reaction temperature was 150° C. and the gauge pressure was 0.6 MPa. Reaction conditions and the measurement result of a concentration of hesperidin and methylhesperidin in the composition are shown in Table 1.

Comparative Examples 4 and 5

A hesperidin composition was obtained as a hesperidin-containing aqueous solution by a same procedure as in Example 4, except that the reaction temperature was 90° C. or 25° C. and the gauge pressure was 0 MPa. Reaction conditions and the measurement result of a concentration of hesperidin and methylhesperidin in the composition are shown in Table 1.

Comparative Example 6

A hesperidin composition was obtained as a hesperidin-containing aqueous solution by a same procedure as in Example 1, except that the EGCG preparation was not added and that the reaction temperature was 25° C. and the gauge pressure was 0 MPa. Reaction conditions and the measurement result of a concentration of hesperidin in the composition are shown in Table 1.

TABLE 1

|  |  |  | Example 1 | Example 2 | Comparative Example 1 | Comparative Example 2 | Example 3 | Comparative Example 3 | Example 4 |
|---|---|---|---|---|---|---|---|---|---|
| Charge | (A) Hardly water-soluble polyphenols |  | Hesperidin | Hesperidin | Hesperidin | Hesperidin | Hesperidin | Hesperidin | Hesperidin |
|  | log P value of (A) |  | −0.24 | −0.24 | −0.24 | −0.24 | −0.24 | −0.24 | −0.24 |
|  | Component (B) |  | EGCG | EGCG | EGCG | EGCG | Chlorogenic acid | Chlorogenic acid | Methylhesperidin |
|  | (A) Charged concentration | [g/L] | 9.00 | 9.00 | 9.00 | 9.00 | 9.00 | 9.00 | 9.00 |
|  | (B) Charged concentration | [g/L] | 4.29 | 4.29 | 4.29 | 4.29 | 4.28 | 4.28 | 4.29 |
|  | (A)/(B) mass ratio | [—] | 2.10 | 2.10 | 2.10 | 2.10 | 2.10 | 2.10 | 2.10 |
| Treatment Conditions | Aqueous medium | [—] | water | water | water | water | water | water | water |
|  | Heating temperature | [° C.] | 120 | 110 | 90 | 70 | 120 | 70 | 120 |
|  | Gauge pressure | [MPa] | 0.3 | 0.3 | 0 | 0 | 0.3 | 0 | 0.3 |
| Analyzed value | (A) concentration (25° C.) | [g/L] | 1.03 | 0.92 | 0.14 | 0.14 | 0.95 | 0.09 | 2.12 |
|  | (B) concentrations (25° C.) | [g/L] | 4.20 | 4.22 | 4.19 | 4.19 | 4.16 | 4.13 | 4.19 |

TABLE 1-continued

| | | | | | | | | | |
|---|---|---|---|---|---|---|---|---|---|
| (A)/(B) mass ratio | [—] | 0.245 | 0.218 | 0.033 | 0.033 | 0.228 | 0.022 | 0.506 | |

| | | | | Example 5 | Comparative Example 4 | Comparative Example 5 | Comparative Example 6 |
|---|---|---|---|---|---|---|---|
| Charge | (A) Hardly water-soluble polyphenols | | | Hesperidin | Hesperidin | Hesperidin | Hesperidin |
| | log P value of (A) | | | −0.24 | −0.24 | −0.24 | −0.24 |
| | Component (B) | | | Methylhesperidin | Methylhesperidin | Methylhesperidin | — |
| | (A) Charged concentration | [g/L] | | 9.00 | 9.00 | 9.00 | 9.00 |
| | (B) Charged concentration | [g/L] | | 4.29 | 4.29 | 4.29 | — |
| | (A)/(B) mass ratio | [—] | | 2.10 | 2.10 | 2.10 | — |
| Treatment Conditions | Aqueous medium | [—] | | water | water | water | water |
| | Heating temperature | [° C.] | | 150 | 90 | 25 | 25 |
| | Gauge pressure | [MPa] | | 0.6 | 0 | 0 | 0 |
| Analyzed value | (A) concentration (25° C.) | [g/L] | | 2.7 | 0.67 | 0.05 | 0.05 |
| | (B) concentrations (25° C.) | [g/L] | | 4.15 | 4.22 | 4.24 | — |
| | (A)/(B) mass ratio | [—] | | 0.651 | 0.159 | 0.012 | — |

Example 6

A quercetin composition was obtained as a quercetin-containing aqueous solution by a same procedure as in Example 1, except that a quercetin preparation (manufactured by Acros Organics Co., quercetin content 95%) was used as the hardly water-soluble polyphenols and that the reaction temperature was 150° C. and the gauge pressure was 0.6 MPa. Reaction conditions and the measurement result of a concentration of quercetin and EGCG in the composition are shown in Table 2.

Comparative Example 7

A quercetin composition was obtained as a quercetin-containing aqueous solution by a same procedure as in Example 6, except that the reaction temperature was 70° C. and the gauge pressure was 0 MPa. Reaction conditions and the measurement result of a concentration of quercetin and EGCG in the composition are shown in Table 2.

Comparative Example 8

A quercetin composition was obtained as a quercetin-containing aqueous solution by a same procedure as in Example 6, except that the EGCG preparation was not added and that the reaction temperature was 25° C. and the gauge pressure was 0 MPa. Reaction conditions and the measurement result of a concentration of quercetin in the composition are shown in Table 2.

TABLE 2

| | | | Example 6 | Comparative Example 7 | Comparative Example 8 |
|---|---|---|---|---|---|
| Charge | (A) Hardly water-soluble polyphenols | | quercetin | quercetin | quercetin |
| | log P value of (A) | | 1.97 | 1.97 | 1.97 |
| | Component (B) | | EGCG | EGCG | — |
| | (A) Charged concentration | [g/L] | 9.50 | 9.50 | 9.50 |
| | (B) Charged concentration | [g/L] | 4.29 | 4.29 | — |
| | (A)/(B) mass ratio | [—] | 2.21 | 2.21 | — |
| Treatment conditions | Aqueous medium | [—] | water | water | water |
| | Heating temperature | [° C.] | 150 | 70 | 25 |
| | Gauge pressure | [MPa] | 0.6 | 0 | 0 |
| Analyzed value | (A) concentration (25° C.) | [g/L] | 0.0116 | 0.0046 | 0.0046 |
| | (B) concentration (25° C.) | [g/L] | 4.20 | 4.20 | — |
| | (A)/(B) mass ratio | [—] | 0.0028 | 0.0011 | — |

Example 7

A resveratrol composition was obtained as a resveratrol-containing aqueous solution by a same procedure as in Example 1, except that a resveratrol preparation (manufactured by Wako Pure Chemical Industries, Ltd., for biochemistry) was used as hardly water-soluble polyphenols at a concentration of 0.72 g/L. Reaction conditions and the measurement result of a concentration of resveratrol and EGCG in the composition are shown in Table 3.

Comparative Example 9

A resveratrol composition was obtained as a resveratrol-containing aqueous solution by a same procedure as in Example 7, except that the reaction temperature was 70° C. and the gauge pressure was 0 MPa. Reaction conditions and the measurement result of a concentration of resveratrol and EGCG in the composition are shown in Table 3.

Comparative Example 10

A resveratrol composition was obtained as a resveratrol-containing aqueous solution by a same procedure as in Example 7, except that the EGCG preparation was not added and that the reaction temperature was 25° C. and the gauge pressure was 0 MPa. Reaction conditions and the measurement result of a concentration of resveratrol in the composition are shown in Table 3.

TABLE 3

|  |  |  | Example 7 | Comparative Example 9 | Comparative Example 10 |
|---|---|---|---|---|---|
| Charge | (A) Hardly water-soluble polyphenols |  | resveratrol | resveratrol | resveratrol |
|  | log P value of (A) |  | 3.08 | 3.08 | 3.08 |
|  | Component (B) |  | EGCG | EGCG | — |
|  | (A) Charged concentration | [g/L] | 0.72 | 0.72 | 0.72 |
|  | (B) Charged concentration | [g/L] | 4.29 | 4.29 | — |
|  | (A)/(B) mass ratio | [—] | 0.168 | 0.168 | — |
| Treatment Conditions | Aqueous medium | [—] | water | water | water |
|  | Heating temperature | [° C.] | 120 | 70 | 25 |
|  | Gauge pressure | [MPa] | 0.3 | 0.3 | 0 |
| Analyzed value | (A) Concentration (25° C.) | [g/L] | 0.128 | 0.060 | 0.058 |
|  | (B) Concentration (25° C.) | [g/L] | 4.19 | 4.20 | — |
|  | (A)/(B) mass ratio | [—] | 0.031 | 0.014 | — |

Example 8

A naringin composition was obtained as a naringin-containing aqueous solution by a same procedure as in Example 1, except that a naringin preparation (manufactured by Acros Organics Co., naringin content 97%, the same shall apply hereafter) was used as hardly water-soluble polyphenols and that the reaction temperature was 150° C. and the gauge pressure was 0.6 MPa. Reaction conditions and the measurement result of a concentration of naringin and EGCG in the composition are shown in Table 4.

Example 9

A naringin composition was obtained as a naringin-containing aqueous solution by a same procedure as in Example 8, except that the reaction temperature was 110° C. and the gauge pressure was 0.3 MPa. Reaction conditions and the measurement result of a concentration of naringin and EGCG in the composition are shown in Table 4.

Comparative Examples 11 and 12

A naringin composition was obtained as a naringin-containing aqueous solution by a same procedure as in Example 8, except that the reaction temperature was 90° C. or 70° C. and the gauge pressure was 0 MPa. Reaction conditions and the measurement result of a concentration of naringin and EGCG in the composition are shown in Table 4.

Example 10

A naringin composition was obtained as a naringin-containing aqueous solution by a same procedure as in Example 1, except that each of the naringin preparation and the methylhesperidin preparation was dispersed at 5 g/L and dissolved at 4.29 g/L, respectively, in distilled water. Reaction conditions and the measurement result of a concentration of naringin and methylhesperidin in the composition are shown in Table 4.

Comparative Example 13

A naringin composition was obtained as a naringin-containing aqueous solution by a same procedure as in Example 10, except that the reaction temperature was 25° C. and the gauge pressure was 0 MPa. Reaction conditions and the measurement result of a concentration of naringin and methylhesperidin in the composition are shown in Table 4.

Comparative Example 14

A naringin composition was obtained as a naringin-containing aqueous solution by a same procedure as in Example 8, except that the EGCG preparation was not added and that the reaction temperature was 25° C. and the gauge pressure was 0 MPa. Reaction conditions and the measurement result of a concentration of naringin in the composition are shown in Table 4.

TABLE 4

|  |  |  | Example 8 | Example 9 | Comparative Example 11 | Comparative Example 12 | Example 10 | Comparative Example 13 | Comparative Example 14 |
|---|---|---|---|---|---|---|---|---|---|
| Charge | (A) Hardly water-soluble polyphenols |  | naringin | naringin | naringin | naringin | naringin | naringin | naringin |
|  | log P value of (A) |  | −0.15 | −0.15 | −0.15 | −0.15 | −0.15 | −0.15 | −0.15 |
|  | Component (B) |  | EGCG | EGCG | EGCG | EGCG | methylhesperidin | methylhesperidin | — |
|  | (A) Charged concentration | [g/L] | 9.70 | 9.70 | 9.70 | 9.70 | 4.85 | 4.85 | 9.70 |
|  | (A) Charged concentration | [g/L] | 4.29 | 4.29 | 4.29 | 4.29 | 4.29 | 4.29 | — |
|  | (A)/(B) mass ratio | [—] | 2.26 | 2.26 | 2.26 | 2.26 | 1.13 | 1.13 | — |
| Treatment Conditions | Aqueous medium | [—] | water | water | water | water | water | water | water |
|  | Heating temperature | [° C.] | 150 | 110 | 90 | 70 | 120 | 25 | 25 |
|  | Gauge pressure | [MPa] | 0.6 | 0.3 | 0 | 0 | 0.3 | 0 | 0 |

TABLE 4-continued

|  |  | Example 8 | Example 9 | Comparative Example 11 | Comparative Example 12 | Example 10 | Comparative Example 13 | Comparative Example 14 |
|---|---|---|---|---|---|---|---|---|
| Analyzed value | (A) concentration [g/L] (25° C.) | 2.30 | 1.9 | 1.1 | 0.97 | 2.34 | 0.71 | 0.44 |
|  | (B) concentration [g/L] (25° C.) | 4.21 | 4.21 | 4.18 | 4.20 | 4.22 | 4.22 | — |
|  | (A)/(B) mass ratio [—] | 0.55 | 0.45 | 0.27 | 0.23 | 0.55 | 0.17 | — |

Example 11

A curcumin composition was obtained as a curcumin-containing aqueous solution by a same procedure as in Example 1, except that a curcumin preparation (manufactured by Wako Pure Chemical Industries, Ltd., special grade reagent) was used as hardly water-soluble polyphenols at a concentration of 10 g/L and that the reaction temperature was 150° C. and the gauge pressure was 0.6 MPa. Reaction conditions and the measurement result of a concentration of curcumin and EGCG in the composition are shown in Table 5.

Comparative Example 15

A curcumin composition was obtained as a curcumin-containing aqueous solution by a same procedure as in Example 11, except that the reaction temperature was 70° C. and the gauge pressure was 0 MPa. Reaction conditions and the measurement result of a concentration of curcumin and EGCG in the composition are shown in Table 5.

Comparative Example 16

A curcumin composition was obtained as a curcumin-containing aqueous solution by a same procedure as in Example 11, except that the EGCG preparation was not added and that the reaction temperature was 25° C. and the gauge pressure was 0 MPa. Reaction conditions and the measurement result of a concentration of curcumin in the composition are shown in Table 5.

Example 12

A rutin composition was obtained as a rutin-containing aqueous solution by a same procedure as in Example 1, except that a rutin preparation (manufactured by Tokiwa Phytochemical Co., Ltd., rutin content 100%, the same shall apply hereafter) was used as hardly water-soluble polyphenols at a concentration of 2 g/L and that a purified green tea extract (an aqueous solution containing 15% of the catechins, a gallate forms ratio 30%) was used as the catechins at a concentration of 28.6 g/L. Reaction conditions and the measurement result of a concentration of rutin and catechins in the composition are shown in Table 6.

Comparative Example 17

A rutin composition was obtained as a rutin-containing aqueous solution by a same procedure as in Example 12, except that the reaction temperature was 70° C. and the gauge pressure was 0 MPa. Reaction conditions and the measurement result of a concentration of rutin and the catechins in the composition are shown in Table 6.

Example 13

A rutin composition was obtained as a rutin-containing aqueous solution by a same procedure as in Example 12, except that a purified coffee bean extract (chlorogenic acids content 40%) was used as chlorogenic acids at a concentration of 10.7 g/L. Reaction conditions and the measurement result of a concentration of rutin and chlorogenic acids in the composition are shown in Table 6.

Comparative Example 18

A rutin composition was obtained as a rutin-containing aqueous solution by a same procedure as in Example 13, except that the reaction temperature was 70° C. and the gauge pressure was 0 MPa. Reaction conditions and the measurement result of a concentration of rutin and chlorogenic acids in the composition are shown in Table 6.

Example 14

A rutin composition was obtained as a rutin-containing aqueous solution by a same procedure as in Example 12, except that a purified green tea extract (an aqueous solution containing 15% of the catechins, gallate forms ratio 30%) was used as the catechins at a concentration of 14.3 g/L and that a purified coffee bean extract (chlorogenic acids content 40%) was used as chlorogenic acids at a concentration of 5.4 g/L. Reaction conditions and the measurement result of a concentration of rutin, the catechins and chlorogenic acids in the composition are shown in Table 6.

Comparative Example 19

A rutin composition was obtained as a rutin-containing aqueous solution by a same procedure as in Example 14,

TABLE 5

|  |  |  | Example 11 | Comparative Example 15 | Comparative Example 16 |
|---|---|---|---|---|---|
| Charge | (A) Hardly water-soluble polyphenols |  | curcumin | curcumin | curcumin |
|  | log P value of (A) |  | 3.29 | 3.29 | 3.29 |
|  | Component (B) |  | EGCG | EGCG | — |
|  | (A) Charged concentration | [g/L] | 10.00 | 10.00 | 10 |
|  | (B) Charged concentration | [g/L] | 4.29 | 4.29 | — |
|  | (A)/(B) mass ratio | [—] | 2.33 | 2.33 | — |
| Treatment conditions | Aqueous medium | [—] | water | water | water |
|  | Heating temperature | [° C.] | 150 | 70 | 25 |
|  | Gauge pressure | [MPa] | 0.6 | 0 | 0 |
| Analyzed value | (A) Concentration (25° C.) | [g/L] | 0.014 | 0.001 | 0.001 |
|  | (B) Concentration (25° C.) | [g/L] | 4.21 | 4.20 | — |
|  | (A)/(B) mass ratio | [—] | 0.0033 | 0.0002 | — | except that the reaction temperature was 70° C. and the gauge pressure was 0 MPa. Reaction conditions and the measurement result of a concentration of rutin, the catechins and chlorogenic acids in the composition are shown in Table 6.

Example 15

A rutin composition was obtained as a rutin-containing aqueous solution by a same procedure as in Example 12, except that a methylhesperidin preparation was used at a concentration of 4.29 g/L instead of the purified green tea extract. Reaction conditions and the measurement result of a concentration of rutin and methylhesperidin in the composition are shown in Table 6.

Comparative Example 20

A rutin composition was obtained as a rutin-containing aqueous solution by a same procedure as in Example 15, except that the reaction temperature was 25° C. and the gauge pressure was 0 MPa. Reaction conditions and the measurement result of a concentration of rutin and methylhesperidin in the composition are shown in Table 6.

Comparative Example 21

A rutin composition was obtained as a rutin-containing aqueous solution by a same procedure as in Example 12, except that the catechins were not added. Reaction conditions and the measurement result of a concentration of rutin in the composition are shown in Table 6.

Comparative Example 22

A rutin composition was obtained as a rutin-containing aqueous solution by a same procedure as in Example 12, except that the catechins were not added and that the reaction temperature was 25° C. and the gauge pressure was 0 MPa. Reaction conditions and the measurement result of a concentration of rutin in the composition are shown in Table 6.

TABLE 6

|  |  |  | Example 12 | Comparative Example 17 | Example 13 | Comparative Example 18 | Example 14 | Comparative Example 19 |
|---|---|---|---|---|---|---|---|---|
| Charge | (A) Hardly water-soluble polyphenols |  | rutin | rutin | rutin | rutin | rutin | rutin |
|  | log P value of (A) |  | −0.33 | −0.33 | −0.33 | −0.33 | −0.33 | −0.33 |
|  | Component (B) |  | purified green tea extract | purified green tea extract | chlorogenic acid | chlorogenic acid | purified green tea extract + chlorogenic acid | purified green tea extract + chlorogenic acid |
|  | Charged concentration of (A) | [g/L] | 2.00 | 2.00 | 2.00 | 2.00 | 2.00 | 2.00 |
|  | Charged concentration of (B) | [g/L] | 4.29 | 4.29 | 4.28 | 4.28 | 4.31 | 4.31 |
|  | (A)/(B) mass ratio | [—] | 0.47 | 0.47 | 0.47 | 0.47 | 0.46 | 0.46 |
| Treatment conditions | Aqueous medium | [—] | water | water | water | water | water | water |
|  | Heating temperature | [° C.] | 120 | 70 | 120 | 70 | 120 | 70 |
|  | Gauge pressure | [MPa] | 0.3 | 0 | 0.3 | 0 | 0.3 | 0 |
| Analyzed value | (A) concentration (25° C.) | [g/L] | 0.135 | 0.044 | 0.105 | 0.057 | 0.13 | 0.08 |
|  | (B) concentration (25° C.) | [g/L] | 4.19 | 4.19 | 4.17 | 4.14 | 4.18 | 4.18 |
|  | (A)/(B) mass ratio | [—] | 0.0322 | 0.0105 | 0.025 | 0.014 | 0.031 | 0.019 |

|  |  |  | Example 15 | Comparative Example 20 | Comparative Example 21 | Comparative Example 22 |
|---|---|---|---|---|---|---|
| Charge | (A) Hardly water-soluble polyphenols |  | rutin | rutin | rutin | rutin |
|  | log P value of (A) |  | −0.33 | −0.33 | −0.33 | −0.33 |
|  | Component (B) |  | methylhesperidin | methylhesperidin | — | — |
|  | Charged concentration of (A) | [g/L] | 2.00 | 2.00 | 2.00 | 2.00 |
|  | Charged concentration of (B) | [g/L] | 4.29 | 4.29 | — | — |
|  | (A)/(B) mass ratio | [—] | 0.47 | 0.47 | — | — |
| Treatment conditions | Aqueous medium | [—] | water | water | water | water |
|  | Heating temperature | [° C.] | 120 | 25 | 120 | 25 |
|  | Gauge pressure | [MPa] | 0.3 | 0 | 0.3 | 0 |

TABLE 6-continued

| | | | | | | |
|---|---|---|---|---|---|---|
| Analyzed value | (A) concentration (25° C.) | [g/L] | 0.28 | 0.07 | 0.037 | 0.028 |
| | (B) concentration (25° C.) | [g/L] | 4.21 | 4.24 | — | — |
| | (A)/(B) mass ratio | [—] | 0.067 | 0.017 | — | — |

Example 16

A ferulic acid composition was obtained as a ferulic acid-containing aqueous solution by a same procedure as in Example 1, except that a ferulic acid preparation (manufactured by Tokyo Chemical Industry Co., Ltd., ferulic acid content 100%) was used as hardly water-soluble polyphenols at a concentration of 6 g/L and that a purified coffee bean extract was used as chlorogenic acids at a concentration of 10.7 g/L. Reaction conditions and the measurement result of a concentration of ferulic acid and chlorogenic acid in the composition are shown in Table 7.

Comparative Examples 23 and 24

A ferulic acid composition was obtained as a ferulic acid-containing aqueous solution by a same procedure as in Example 16, except that the reaction temperature was 70° C. or 25° C. and the gauge pressure was 0 MPa. Reaction conditions and the measurement result of a concentration of ferulic acid and chlorogenic acid in the composition are shown in Table 7.

TABLE 7

| | | | Example 16 | Comparative Example 23 | Comparative Example 24 |
|---|---|---|---|---|---|
| Charge | (A) Hardly water-soluble polyphenols | | ferulic acid | ferulic acid | ferulic acid |
| | log P value of (A) | | 1.51 | 1.51 | 1.51 |
| | Component (B) | | chlorogenic acid | chlorogenic acid | chlorogenic acid |
| | (A) Charged concentration | [g/L] | 6.00 | 6.00 | 6.00 |
| | (B) Charged concentration | [g/L] | 4.28 | 4.28 | 4.28 |
| | (A)/(B) mass ratio | [—] | 1.40 | 1.40 | 1.40 |
| Treatment conditions | Aqueous medium | [—] | water | water | water |
| | Heating temperature | [° C.] | 120 | 70 | 25 |
| | Gauge pressure | [MPa] | 0.3 | 0 | 0 |
| Analyzed value | (A) Concentration (25° C.) | [g/L] | 6.00 | 2.42 | 1.61 |
| | (B) Concentration (25° C.) | [g/L] | 4.19 | 4.16 | 4.16 |
| | (A)/(B) mass ratio | [—] | 1.43 | 0.58 | 0.39 |

Example 17

A caffeic acid composition was obtained as a caffeic acid-containing aqueous solution by a same procedure as in Example 1, except that a caffeic acid preparation (manufactured by Tokyo Chemical Industry Co., Ltd., caffeic acid content 100%) was used as hardly water-soluble polyphenols at a concentration of 6 g/L and that a purified coffee bean extract was used as chlorogenic acids at a concentration of 10.7 g/L. Reaction conditions and the measurement result of a concentration of caffeic acid and chlorogenic acid in the composition are shown in Table 8.

Comparative Examples 25 and 26

A caffeic acid composition was obtained as a caffeic acid containing aqueous solution by a same procedure as in Example 17, except that the reaction temperature was 80° C. or 25° C. and the gauge pressure was 0 MPa. Reaction conditions and the result of the measurement of concentration of caffeic acid and chlorogenic acid in the composition are shown in Table 8.

TABLE 8

| | | | Example 17 | Comparative Example 25 | Comparative Example 26 |
|---|---|---|---|---|---|
| Charge | (A) Hardly water-soluble polyphenols | | caffeic acid | caffeic acid | caffeic acid |
| | log P value of (A) | | 1.15 | 1.15 | 1.15 |
| | Component (B) | | chlorogenic acid | chlorogenic acid | chlorogenic acid |
| | (A) Charged concentration | [g/L] | 6.00 | 6.00 | 6.00 |
| | (B) Charged concentration | [g/L] | 4.28 | 4.28 | 4.28 |
| | (A)/(B) mass ratio | [—] | 1.40 | 1.40 | 1.40 |
| Treatment conditions | Aqueous medium | [—] | water | water | water |
| | Heating temperature | [° C.] | 120 | 80 | 25 |
| | Gauge pressure | [MPa] | 0.3 | 0 | 0 |
| Analyzed value | (A) Concentration (25° C.) | [g/L] | 6.00 | 2.79 | 0.88 |
| | (B) Concentration (25° C.) | [g/L] | 4.16 | 4.13 | 4.16 |
| | (A)/(B) mass ratio | [—] | 1.44 | 0.68 | 0.21 |

As is clearly shown in Tables 1 to 8, it was possible to obtain the polyphenol composition with a high content of hardly water-soluble polyphenols, whereby significant increase of the solubility of hardly water-soluble polyphenols has been achieved.

Furthermore, the compositions obtained had no strange odor such as grain smell. The compositions including the catechins and chlorogenic acids had a moderate bitterness derived from these components. They also had a taste and flavor suitable for various foods and drinks and pharmaceuticals, especially for functional beverages.

Example 18

Each of a hesperidin preparation and a monoglucosylhesperidin preparation (Hayashibara Hesperidin S (trade name), manufactured by Hayashibara Biochemical Laboratories, Inc., hesperidin content 17 mass %), monoglucosylhesperidin content 74 mass %, the same shall apply hereafter) was dispersed at a concentration of 10.0 g/L and dissolved at a concentration of 4.3 g/L, respectively, in distilled water, and homogeneously stirred in a slurry supply tank. The solution in the slurry supply tank was fed to a stainless steel flow-type reactor with inner volume of 100 mL (manufactured by Nitto Koatsu Co., Ltd.) at a flow rate of 100 mL/min, and the reaction was carried out at 120° C. (average residence time 1 minute). Pressure was adjusted to 1.5 MPa by an outlet valve. Reaction solution was taken out through the reactor outlet, cooled to room temperature (25° C.) and recovered to a reaction solution recovery tank. The cooling was performed by a continuous heat exchange with coolant water, passing the reaction solution taken out through the outlet of the flow-type reactor to a dual pipe cooler.

The recovered reaction solution was stirred for 3 days at room temperature. Solids were then filtered off to obtain the hesperidin composition as a hesperidin-containing aqueous solution. Reaction conditions and the measurement result of a concentration of hesperidin (HES) and monoglucosylhesperidin (mGHES) in the composition are shown in Table 9 (the same shall apply hereafter).

Example 19

A hesperidin composition was obtained as a hesperidin-containing aqueous solution by a same procedure as in Example 18, except that the reaction temperature was 150° C. In addition, a powdery hesperidin composition was obtained by a freeze-drying to remove water. It has found that the powdery hesperidin composition redissolves in water (25° C.) even at a concentration of 10 g/L.

Example 20

A hesperidin composition was obtained as a hesperidin-containing aqueous solution by a same procedure as in Example 18, except that the reaction temperature was 180° C.

Example 21

A hesperidin composition was obtained as a hesperidin-containing aqueous solution by a same procedure as in Example 19, except that a concentration of the monoglucosylhesperidin preparation in distilled water was 1.1 g/L.

Example 22

A hesperidin composition was obtained as a hesperidin-containing aqueous solution by a same procedure as in Example 19, except that a concentration of the hesperidin preparation in distilled water was 20 g/L.

Comparative Example 27

A hesperidin composition was obtained as a hesperidin-containing aqueous solution by a same procedure as in Example 18, except that the reaction temperature was 25° C.

Comparative Example 28

A hesperidin composition was obtained as a hesperidin-containing aqueous solution by a same procedure as in Example 18, except that the reaction temperature was 90° C.

Example 23

A hesperidin composition was obtained as a hesperidin-containing aqueous solution by a same procedure as in Example 18, except that a concentration of the monoglucosylhesperidin preparation in distilled water was 10 g/L.

Example 24

A hesperidin composition was obtained as a hesperidin-containing aqueous solution by a same procedure as in Example 23, except that the reaction temperature was 150° C.

Example 25

A hesperidin composition was obtained as a hesperidin-containing aqueous solution by a same procedure as in Example 23, except that the reaction temperature was 180° C.

Comparative Example 29

A hesperidin composition was obtained as a hesperidin-containing aqueous solution by a same procedure as in Example 23, except that the reaction temperature was 90° C.

The mass ratio of HES relative to mGHES in the hesperidin composition obtained in Examples 18 to 25 and Comparative Examples 27 to 29 is shown in Table 9.

TABLE 9

| | | | Example 18 | Example 19 | Example 20 | Example 21 | Example 22 | Example 23 |
|---|---|---|---|---|---|---|---|---|
| Charge | Hesperidin preparation * | [g/L] | 10.0 | 10.0 | 10.0 | 10.0 | 20.0 | 10.0 |
| | monoglucosyl-hesperidin preparation ** | [g/L] | 4.3 | 4.3 | 4.3 | 1.1 | 4.3 | 10.0 |
| Treatment conditions | Aqueous medium | [—] | water | water | water | water | water | water |
| | Temperature | [° C.] | 120 | 150 | 180 | 150 | 150 | 120 |
| | Pressure | [MPa] | 1.5 | 1.5 | 1.5 | 1.5 | 1.5 | 1.5 |
| Analyzed value | HES | [g/L] | 2.29 | 2.11 | 2.08 | 1.31 | 3.07 | 3.06 |
| | mGHES | [g/L] | 3.04 | 2.18 | 2.14 | 0.41 | 1.85 | 7.37 |
| | HES/mGHES | [g/g] | 0.75 | 0.97 | 0.97 | 3.21 | 1.67 | 0.42 |

| | | | Example 24 | Example 25 | Comparative Example 27 | Comparative Example 28 | Comparative Example 29 |
|---|---|---|---|---|---|---|---|
| Charge | Hesperidin preparation * | [g/L] | 10.0 | 10.0 | 10.0 | 10.0 | 10.0 |
| | monoglucosyl- | [g/L] | 10.0 | 10.0 | 4.3 | 4.3 | 10.0 |

TABLE 9-continued

|  |  |  |  |  |  |  |  |
|---|---|---|---|---|---|---|---|
|  | hesperidin preparation ** |  |  |  |  |  |  |
| Treatment conditions | Aqueous medium | [—] | water | water | water | water | water |
|  | Temperature | [° C.] | 150 | 180 | 25 | 90 | 90 |
|  | Pressure | [MPa] | 1.5 | 1.5 | 1.5 | 1.5 | 1.5 |
| Analyzed value | HES | [g/L] | 3.04 | 2.86 | 0.46 | 0.65 | 1.28 |
|  | mGHES | [g/L] | 5.80 | 5.54 | 3.25 | 3.09 | 7.31 |
|  | HES/mGHES | [g/g] | 0.52 | 0.52 | 0.19 | 0.21 | 0.17 |

\* Hesperidin "Hamari" (trade name), Hamari Chemicals, Ltd.
\*\* Hayashibara Hesperidin S (trade name), Hayashibara Biochemical Laboratories, Inc.

As is clearly shown in Table 9, it was possible to obtain the hesperidin composition with a high content of hesperidin by a heat treatment of hesperidin and hesperidin sugar adduct at from 100 to 180° C., whereby significant increase of the solubility of hesperidin has been achieved.

Example 26

A hesperidin composition was obtained as a hesperidin-containing aqueous solution by a same procedure as in Example 19, except that a 50 vol % aqueous ethanol solution was used instead of distilled water as the aqueous medium to disperse the hesperidin preparation or to dissolve the monoglucosylhesperidin preparation. The measurement result of a concentration of HES and mGHES in the composition is shown in Table 10 (the same shall apply hereafter).

Comparative Example 30

A hesperidin composition was obtained as a hesperidin-containing aqueous solution by a same procedure as in Example 26, except that the reaction temperature was 25° C.

The mass ratio of HES relative to mGHES in the hesperidin composition obtained in Example 26 and Comparative Example 30 is shown in Table 10.

TABLE 10

|  |  |  | Example 26 | Comparative Example 30 |
|---|---|---|---|---|
| Charge | Hesperidin preparation * | [g/L] | 10.0 | 10.0 |
|  | Monoglucosyl-hesperidin preparation ** | [g/L] | 4.3 | 4.3 |
| treatment conditions | Aqueous medium | [—] | 50 vol % ethanol | 50 vol % ethanol |
|  | Temperature | [° C.] | 150 | 25 |
|  | Pressure | [MPa] | 1.5 | 1.5 |
| Analyzed value | HES | [g/L] | 5.13 | 0.48 |
|  | mGHES | [g/L] | 3.01 | 3.01 |
|  | HES/mGHES | [g/g] | 1.71 | 0.16 |

\* Hesperidin "Hamari" (trade name), Hamari Chemicals, Ltd.
\*\* Hayashibara Hesperidin S (trade name), Hayashibara Biochemical Laboratories, Inc.

As is clearly shown in Table 10, it was possible to obtain the hesperidin composition with a high content of hesperidin by using an aqueous solution containing an organic solvent as the aqueous medium for the reaction.

Example 27

A hesperidin composition was obtained as a hesperidin-containing aqueous solution by a same procedure as in Example 18, except that a soy sauce (pH 4.9, manufactured by Yamasa Corporation) was used instead of distilled water. The measurement result of a concentration of HES and mGHES in the composition is shown in Table 11 (the same shall apply hereafter).

Example 28

A hesperidin composition was obtained as a hesperidin-containing aqueous solution by a same procedure as in Example 18, except that a low-salt soy sauce (pH 4.7, manufactured by Yamasa Corporation) was used instead of distilled water and that the pressure was 0.3 MPa.

Example 29

A hesperidin composition was obtained as a hesperidin-containing aqueous solution by a same procedure as in Example 18, except that a seasoned ponzu sauce (pH 2.0, manufactured by Mizkan Group Corporation) was used instead of distilled water and that the pressure was 0.3 MPa.

TABLE 11

|  |  |  | Example 27 | Example 28 | Example 29 |
|---|---|---|---|---|---|
| Charge | Hesperidin preparation * | [g/L] | 10.0 | 10.0 | 10.0 |
|  | Monoglucosyl-hesperidin preparation ** | [g/L] | 4.3 | 4.3 | 4.3 |
| Treatment conditions | Aqueous medium | [—] | soy sauce | low-salt soy sauce | ponzu sauce |
|  | Temperature | [° C.] | 120 | 120 | 120 |
|  | Pressure | [MPa] | 1.5 | 0.3 | 0.3 |
| Analyzed value | HES | [g/L] | 1.97 | 2.87 | 2.06 |
|  | mGHES | [g/L] | 3.02 | 3.04 | 3.07 |
|  | HES/mGHES | [g/g] | 0.65 | 0.94 | 0.67 |

\* Hesperidin "Hamari" (trade name), Hamari Chemicals, Ltd.
\*\* Hayashibara Hesperidin S (trade name), Hayashibara Biochemical Laboratories, Inc.

As is clearly shown in Table 11, it was also possible to obtain the hesperidin composition with a high content of hesperidin by using an aqueous medium containing a solute such as amino acid or a salt.

Example 30

A hesperidin composition was obtained as a hesperidin-containing aqueous solution by a similar procedure as in Example 18, except that the pressure was 0.3 MPa. The cooling rate was 7.06° C./s by calculating the cooling time from 120° C. to 90° C. The measurement result of a concentration of HES and mGHES in the composition is shown in Table 12 (the same shall apply hereafter).

Example 31

A hesperidin composition was obtained as a hesperidin-containing aqueous solution by a similar procedure as in Example 30, except that the temperature and flow rate of the cooling water was changed so that the cooling rate calculated from the cooling time from 120° C. to 90° C. was adjusted to 0.52° C./s.

TABLE 12

|  |  |  | Example 30 | Example 31 |
|---|---|---|---|---|
| Charge | Hesperidin preparation * | [g/L] | 10.0 | 10.0 |
|  | monoglucosyl-hesperidin preparation ** | [g/L] | 4.3 | 4.3 |
| Treatment conditions | Aqueous medium | [—] | water | water |
|  | Temperature | [° C.] | 120 | 120 |
|  | Pressure | [MPa] | 0.3 | 0.3 |
|  | Cooling rate | [° C./s] | 7.06 | 0.52 |
| Analyzed value | HES | [g/L] | 2.82 | 1.11 |
|  | mGHES | [g/L] | 3.04 | 2.73 |
|  | HES/mGHES | [g/g] | 0.93 | 0.41 |

* Hesperidin "Hamari" (trade name), Hamari Chemicals, Ltd.
** Hayashibara Hesperidin S (trade name), Hayashibara Biochemical Laboratories, Inc.

The invention claimed is:

1. A method for producing a hesperidin composition, the method comprising:
   subjecting hesperidin and hesperidin sugar adduct to a heat treatment at from 100 to 180° C. in the presence of an aqueous medium, thereby obtaining a heated reaction solution, and
   cooling the heated reaction solution at a cooling rate of 1° C./s or more and 100° C./s or less, thereby obtaining a cooled reaction solution comprising the hesperidin composition.

2. The method for producing the hesperidin composition according to claim 1, wherein the hesperidin sugar adduct is glucosylhesperidin.

3. The method for producing the hesperidin composition according to claim 1, wherein the hesperidin sugar adduct is monoglucosylhesperidin.

4. The method for producing the hesperidin composition according to claim 1, wherein the heat treatment is carried out at a temperature of from 110 to 170° C.

5. The method for producing the hesperidin composition according to claim 1, wherein the mass ratio of hesperidin to hesperidin sugar adduct is from 0.1 to 20 in the heat treatment.

6. The method for producing the hesperidin composition according to claim 1, wherein the aqueous medium is water or an aqueous solution comprising an alcohol having 4 or less carbon atoms.

7. The method for producing the hesperidin composition according to claim 1, further comprising:
   removing a solid from the cooled reaction solution.

8. The method for producing the hesperidin composition according to claim 1, wherein a form of the hesperidin composition after the cooling is an aqueous solution or a powder.

9. The method of claim 8, further comprising removing water from the cooled reaction solution, thereby obtaining the hesperidin composition in the form of a powder.

10. The method of claim 1, wherein the mass ratio of hesperidin to hesperidin sugar adduct is from 0.52 to 3.21 in the heat treatment.

11. The method of claim 1, wherein a content of hesperidin in the cooled reaction solution is from 1.31 to 5.13 g/L.

* * * * *